(12) United States Patent
Curiel

(10) Patent No.: US 6,555,368 B1
(45) Date of Patent: Apr. 29, 2003

(54) CAPSID-MODIFIED RECOMBINANT ADENOVIRUS AND METHODS OF USE

(75) Inventor: David T. Curiel, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/668,791

(22) Filed: Sep. 22, 2000

Related U.S. Application Data

(60) Provisional application No. 60/156,104, filed on Sep. 24, 1999, now abandoned.

(51) Int. Cl.$^7$ .................. C12N 15/00; C12N 15/63; C12N 15/86; C07H 21/04
(52) U.S. Cl. .................. 435/320.1; 435/455; 435/456; 536/23.1; 536/23.4
(58) Field of Search .................. 514/44; 435/320.1, 435/455, 456, 235.1; 536/23.1, 23.4, 23.72

(56) References Cited

U.S. PATENT DOCUMENTS

| | | | |
|---|---|---|---|
| 5,723,287 A | 3/1998 | Russell | 435/5 |
| 5,846,782 A | 12/1998 | Wickham et al. | 435/697 |
| 5,871,727 A | 2/1999 | Curiel | 424/93.2 |

FOREIGN PATENT DOCUMENTS

| | | |
|---|---|---|
| GB | 99/36545 | 7/1999 |

OTHER PUBLICATIONS

Meng et.al.; Tumor Suppressor Genes as Targets for Cancer Gene Therapy, 1999, Gene Therapy of Cancer: 3–20.*
Miller et al.; Targeted vectors for gene therapy, 1995, FASEB J. 9: 190–199.*
Deonarain; Ligand–targeted receptor–mediated vectors for gene delivery, 1998, Exp. Opin. Ther. Patents 8(1):53–69.*
Rudinger; Characteristics of the amino acids as components of a peptide hormone sequence, 1976. In: Peptide Hormones (Parsons, J.A., ed.) University Park Press, Baltimore, pp. 1–7.*
Ngo et.al.; Computational Complexity, Protein Structure Prediction, and the Levinthal Paradox, 1994. In: The Protein Folding Problem and Tertiary Structure Prediction (Merz etal., eds.) Birkhauser, Boston, pp. 419–494.*
Manuel Rosa–Calatrava etal Functional Analysis of Adenovirus Protein IX Identifies Domains Involved in Capsid Stability, Transcriptional Activity, and Nuclear Reorganization Journal Of Virology Aug. 2001 pp. 7131–7141 vol. 75, No. 15.*
Curiel, D., *Strategies to Adapt Adenoviral Vectors for Targeted Delivery.* Ann. NY Acad. Sci. vol. 886, 1999, pp. 158–171.
Verma, et al. *Gene Therapy—Promises, Problems and Prospects.* Nature, vol. 389, 1997, pp. 239–242.
Dang, et al. *Gene Therapy and Translational Cancer Research.* Clinical Cancer Research. vol. 5, 1999, pp. 471–474.
Peng, et al. *Viral Vector Targeting.* Current Opinion in Biotechnology. vol. 10, 1999, pp. 454–457.
Krasnykh, V., et al. *Generation of Recombinant Adenovirus Vectors With Modified Fibers for Altering Viral Tropism.* Journal of Virology vol. 70, 1996, pp. 6839–6846.
Wickham, T., et al. *Targeted Adenovirus–Mediated Gene Delivery to T Cells Via CD3.* Journal of Virology vol. 71, 1997, pp. 7663–7669.
Wickham, T., et al. *Targeted Adenovirus Gene Transfer to Endothelial and Smooth Muscle Cells by Using Bispecific Antibodies.* Journal of Virology vol. 70, 1996, pp. 6831–6838.
Douglas, J., et al. *A System for the Propagation of Adenoviral Vectors With Genetically Modified Receptor Specificities.* Nature Biotechnology vol. 17, 1999, pp. 470–475.

* cited by examiner

Primary Examiner—Dave T. Nguyen
Assistant Examiner—Quang Nguyen
(74) Attorney, Agent, or Firm—Benjamin Aaron Adler

(57) ABSTRACT

The present invention describes a recombinant adenoviral vector in which a single-chain antibody has been introduced into the minor capsid proteins, pIIha or pIX, so that the adenoviral vector can be targeted to a particular cell type. Additionally disclosed is a method of using the recombinant adenoviral vector in targeted gene therapy.

9 Claims, 9 Drawing Sheets

CAPSID-MODIFIED RECOMBINANT ADENOVIRUS AND METHODS OF USE

CROSS-REFERENCE TO RELATED APPLICATION

This non-provisional patent application claims benefit of provisional patent application U.S. Ser. No. 60/156,104, filed Sep. 24, 1999, now abandoned.

FEDERAL FUNDING LEGEND

This invention was produced in part using funds obtained through grant CA82961 from the National Institutes of Health. Consequently, the federal government has certain rights in this invention.

BACKGROUND OF THE INVENTION

1. Field of the Invention

The present invention relates generally to adenoviral gene therapy vectors. More specifically, the present invention relates to adenoviral gene therapy vectors in which the adenoviral tropism has been genetically modified.

2. Description of the Related Art

Adenoviral vectors (Ad) have proven to be of enormous utility for a variety of gene therapy applications. This usefulness is derived largely from the unparalleled delivery efficiency of these vectors for in vitro and in vivo applications. Despite this property, however, the full benefit of these vectors is undermined currently by the lack of cell-specific gene delivery capability. Specifically, the promiscuous tropism of the adenovirus hinders gene delivery in a targeted, cell-specific manner. Thus, for the many gene therapy applications where such cell-specific transduction is required, current adenoviral vectors have limited utility.

To address the issue of efficient, cell-specific gene delivery, a variety of strategies have been developed to alter adenoviral tropism. These approaches have included direct chemical modifications of the adenoviral capsid proteins, bi-specific complexes (e.g., a capsid protein and a targeting moiety), and genetic capsid modifications (e.g., genetic replacement/insertion). Whereas the former two strategies have established the feasibility of adenoviral re-targeting, practical production issues as well as regulatory approval considerations have placed the utmost importance on the approach in which modifications to the adenoviral tropism are introduced genetically.

To this end, methods that alter adenoviral tropism via modifications of the adenoviral major capsid proteins, fiber, penton and hexon, have expanded tropism such that it is independent of the native adenoviral receptor (CAR). These methods additionally may ablate the native tropism of the adenovirus. Experimentally, tropism expansion has been achieved via the incorporation of peptide ligands with specificity for target cellular markers. This has largely been via the incorporation of the peptide, RGD-4C, at fiber and hexon locales. RGD-4C recognizes integrins of the $\alpha v \beta 3$ and $\alpha v \beta 5$ class. In addition, other small peptide markers have been employed to the same end. These studies have established that genetic modification(s) to the capsid can indeed alter adenoviral vector tropism to achieve a limited and/or specific range of gene delivery.

Of note, the locales employed in the context of modifying the major capsid proteins for targeting purposes have allowed only the incorporation of small peptides. To date, these have consisted of peptides identified via phage display methods, or short physiologic peptide ligands. Both of these types of targeting motifs, however, are suboptimal with respect to accomplishing the goal of cell-specific delivery. With respect to the former, only a n extremely limited repertoire of useful peptides have been identified heretofore via phage display techniques. In addition, these peptides have tended to be of low affinity. Furthermore, the fidelity of such targeting peptides, when in the context of the adenoviral vector, is not always preserved. With respect to the latter, available physiologic peptides do not allow targeting to the range of cells required for practical gene therapy approaches.

In this regard, single chain antibodies (scFvs) represent motifs with highly diverse specificities that can be exploited for adenoviral targeting. In addition, single chain antibodies possess high affinities for cognate targets. On this basis, the ability to incorporate single chain antibodies into the adenoviral capsid, and for the single chain antibody specificity/affinity to be preserved following display of the chimeric/recombinant capsid protein would dramatically enhance the utility of genetic capsid modification methods for adenoviral retargeting. The inability to configure single chain antibodies at fiber, hexon, and penton locales has indicated the need to examine the ability of single chain antibodies to be incorporated into alternate capsid proteins.

Thus, the prior art is deficient in alternate adenoviral capsid proteins that allows for the genetic introduction of a useful targeting moiety. The present invention fulfills this long-standing need and desire in the art.

SUMMARY OF THE INVENTION

The present invention describes incorporation of targeting peptides such as single chain antibodies into the "minor" capsid proteins, pIIIa and pIX of adenovirus. pIIIa and pIX are present on the adenoviral capsid as monomers and the proteins have extended amino-terminus ectodomains. Thus, both locale and structural considerations indicate that pIIIa and pIX are the ideal capsid proteins for incorporating single chain antibodies and other targeting peptides and achieving genetic modification and retargeting of the adenovirus.

One object of the present invention is to provide a genetically modified adenovirus vector with cell-specific targeting capability and methods of making this genetically modified adenovirus vector.

In one embodiment of the present invention, there is provided a recombinant adenovirus, wherein the adenovirus comprises a modified gene encoding a modified adenoviral capsid protein.

In another embodiment of the present invention, a method of providing gene therapy to an individual in need of such treatment is described, comprising the steps of: administering to the individual an effective amount of a recombinant adenovirus, wherein the adenovirus comprises a modified gene encoding a modified adenoviral capsid protein.

In yet another embodiment of the present invention, there is provided a method of increasing the ability of an adenovirus to transduce a specific cell type, comprising the step of: modifying a gene encoding an adenoviral capsid protein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

Figure 1:
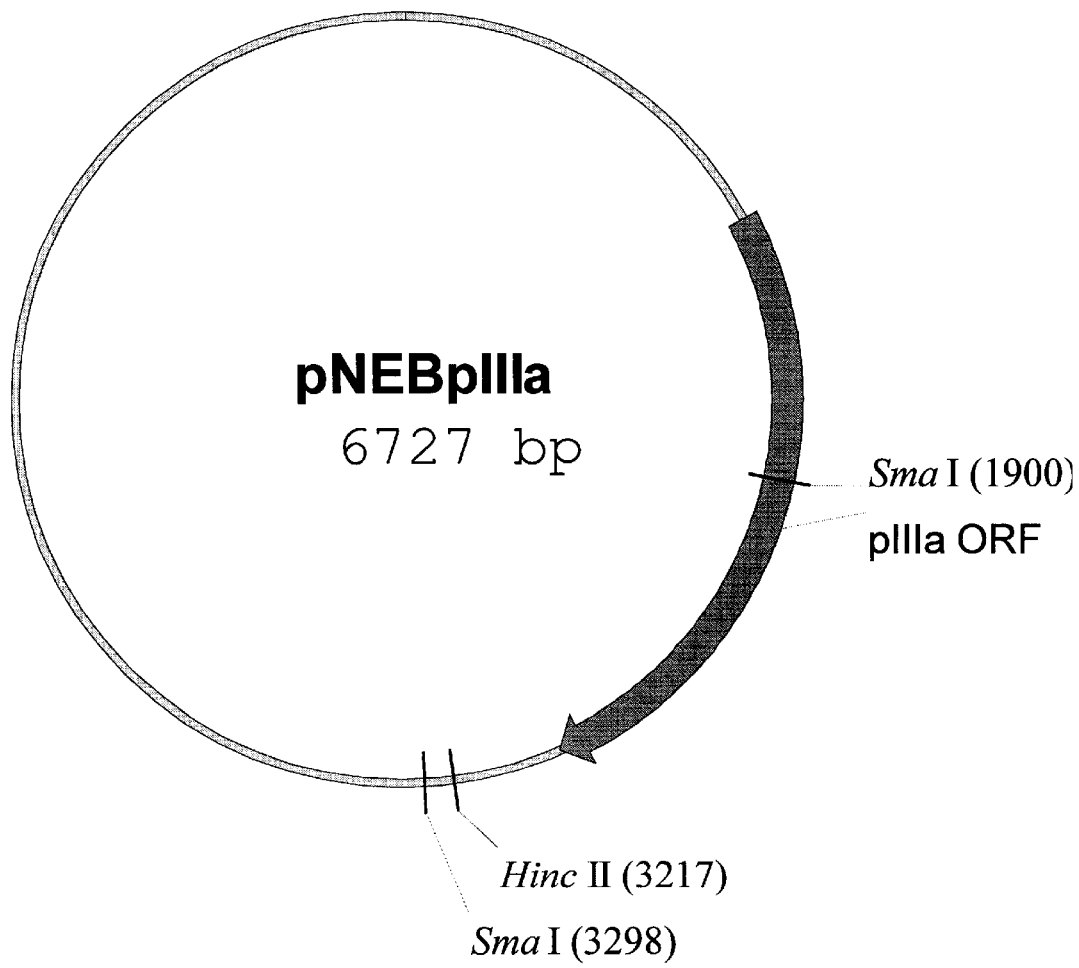
FIG. 1 shows the diagram of plasmid pNEBpIIIa.

The present invention describes incorporation of single chain antibodies and other targeting peptides into alternate capsid proteins. In this regard, the adenovirus contains several "minor" capsid proteins in addition to the fiber, hexon and penton major capsid proteins. To be useful for adenoviral re-targeting purposes, candidate capsid proteins must possess domains that are associated with the surface of the adenoviral virion. Two such capsid proteins are pIX and pIIIa. Thus, of the available minor capsid proteins, pIX and pIIa exhibit unique structural characteristics consistent with the requirements of adenoviral retargeting via genetic capsid modification. Of these two candidate proteins, the multimeric nature of pIX would potentially confound genetic modification strategies on the basis of structural considerations. On the other hand, pIIIa is present on the capsid as a monomer and the protein has an extended amino-terminus ectodomain. Thus, both locale, structure of the protein itself and structural configuration of the protein on the adenoviral capsid point to pIIIa and pIX as candidate capsid proteins for incorporation of scFvs to thereby achieve genetic modification and retargeting.

The present invention is directed towards genetically modified adenovirus vectors and methods of making the same.

The present invention is also directed towards a recombinant adenovirus, wherein the adenovirus comprises a modified gene encoding an adenoviral capsid protein.

In instances when the recombinant adenovirus further comprises a therapeutic gene, the present invention is additionally directed towards a method of providing gene therapy to an individual in need of such treatment, comprising the steps of: administering to the individual an effective amount of a recombinant adenovirus, wherein the adenovirus comprises a modified gene encoding an adenoviral capsid protein. A representative means of administration is systemically, and a preferred therapeutic gene encodes a herpes simplex virus-thymidine kinase. When the above-embodied therapeutic gene encodes a herpes simplex virus-thymidine kinase or other anti-cancer genes which could be used in a similar manner as would be recognized by a person having ordinary skill in this art, the instant invention is still further directed towards a method of killing tumor cells in an individual in need of such treatment, comprising the steps of: administering to the individual an effective amount of the appropriate recombinant adenovirus; and treating the individual with ganciclovir.

The present invention is still further directed towards a method of increasing the ability of an adenovirus to transduce a specific cell type, comprising the step of: modifying a gene encoding an adenoviral capsid protein.

Typically, the gene encoding the capsid protein is modified by introducing a single chain antibody and other targeting peptide into the gene. Preferably, the single chain antibody is directed towards a protein specific to a cell type, and more preferably, the protein is a cell-surface protein. Generally, the cell type is a tumor cell. The present invention also provides for a recombinant adenovirus described herein containing a modified gene encoding a capsid protein and further comprising a therapeutic gene.

Preferably, the capsid gene is a minor capsid gene, and more preferably, the minor capsid genes are pIIIa and pIX. Generally, the modified capsid protein retains its native display profile. Typically, the recombinant adenovirus comprising the modified capsid gene exhibits CAR-independent gene transfer. Additionally, the present invention is directed towards a recombinant adenovirus comprising the modified capsid gene and further comprising an additional modification to an adenovirus fiber knob, wherein the modification to the fiber knob thereby ablates the native tropism of the adenovirus.

It will be apparent to one skilled in the art that various substitutions and modifications may be made to the invention disclosed herein without departing from the scope and spirit of the invention.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984).

It is specifically contemplated that pharmaceutical compositions may be prepared using the novel genetically modified adenoviral vector of the present invention. In such a case, the pharmaceutical composition comprises the novel genetically modified adenoviral vector of the present invention and a pharmaceutically acceptable carrier. A person having ordinary skill in this art would readily be able to determine, without undue experimentation, the appropriate dosages and routes of administration of this genetically modified adenoviral vector of the present invention. When used in vivo for therapy, the genetically modified adenoviral vector of the present invention is administered to the patient or an animal in therapeutically effective amounts, i.e., amounts that eliminate or reduce the tumor burden. It will normally be administered parenterally, preferably intravenously, but other routes of administration will be used as appropriate.

The dose and dosage regimen will depend upon the nature of the cancer (primary or metastatic) and its population, the characteristics of the particular genetically modified adenoviral vector, e.g., its therapeutic index, the patient, the patient's history and other factors. The amount of genetically modified adenoviral vector administered will typically be in the range of about $10^9$ to about $10^{12}$ particles.

The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference.

For parenteral administration, the genetically modified adenoviral vector will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles, such as fixed oils and ethyl oleate, may also be used. Liposomes may be used as carriers. The vehicle may contain minor amounts of additives, such as substances that enhance isotonicity and chemical stability, e.g., buffers and preservatives. The genetically modified adenoviral vector will typically be formulated in such vehicles at concentrations of about $10^9$ to about $10^{12}$ particles.

EXAMPLE 1

Genetic Modification of IIIa Protein of Adenovirus Capsid

Being adenovirus capsid proteins, pIIIa and pIX may be used as a carrier of heterologous peptide sequences, which may serve as purification tags or targeting ligands and, therefore, be utilized for virus purification or/and targeting. For the initial proof of concept, a six-His tag was incorporated into the amino-terminus of pIIIa, and a small 8-amino acid peptide tag—Flag (Asp Tyr Lys Asp Asp Asp Asp Lys, SEQ ID No. 1) was incorporated into the carboxy-terminus of pIX. The possibility to purify the modified viruses by binding to relevant affinity medium was demonstrated.

EXAMPLE 2

Construction of Recombinant Plasmids

In order to generate the shuttle vector for the modification of pIIIa gene, PmII-fragment DNA (4055 bp) from plasmid pTG36021 containing complete Ad5 genome was cloned between SmaI and HincII sites in the plasmid pNEB193. Correct orientation of PmII-fragment containing pIIIa-gene in the context of pNEB193 was confirmed by restriction analysis and constructed plasmid was designated pNEBpIIIa (FIG. 1).

To introduce six histidine tag into the amino-terminal part of pIIIa protein, PCR was perform using PmII-fragment DNA as a template and two pairs of primers: 1) pIIIaN.F: 5'-CGCGAGGAGGTGGCTATAGGACTGA (SEQ ID No. 2), pIIIaN6His.L: 5'-ATGGTGATGGTGATGGTGCATCT-GATCAGAAACATC (SEQ ID No. 3); 2) pIIIaN.R: 5'-TTCGGCCAGCGCGTTTACGATC (SEQ ID No. 4), pIIIaN6His.U: 5'-CACCATCACCATCACCATATGCAA-GACGCAAC (SEQ ID No. 5).

Primers pIIIaN6His.U and pIIIaN6His.L were designed to be partially complementary to the 5'-end of the pIIIa gene and to encode 6His. DNA products, 7440 and 261 bp, generated after first PCR were joined by second PCR.using primers pIIIaN.F and pIIIaN.R, thereby generating DNA fragment (983 bp) corresponding for 5'-terminal portion of pIIIha gene with sequence coding for 6His introduced right after ATG codon.

Figure 2:
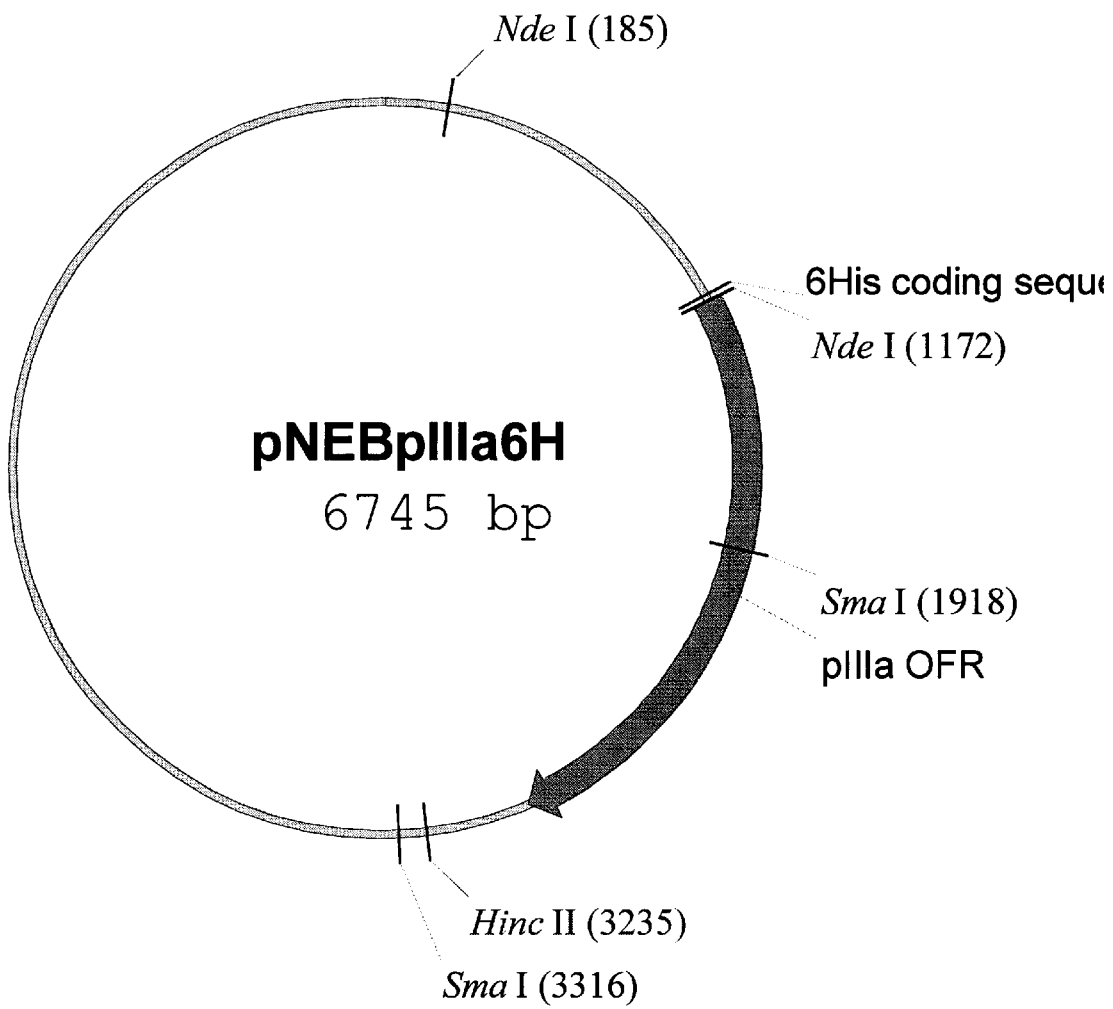
FIG. 2 shows the diagram of plasmid pNEBpIIIa6H.

To insert the modified part of the gene into the shuttle vector, pNEBpIIIa was digested with MluI and BsmI, the vector part was purified and then ligated with corresponding MluI-BsmI-fragment (738 bp) of PCR product. After transformation of *E.coli* with ligation mix, plasmid clones were analyzed for presence of MluI-BsmI-fragment. Confirmation for the correct structure of cloned PCR-originated DNA sequence coding for 6His tag was done by sequence analysis. Plasmid containing correct 6His-coding sequence was designated pNEBpIIIa6H (FIG. 2) and used as a shuttle vector to introduce the modification into Ad5 genome.

Figure 3:
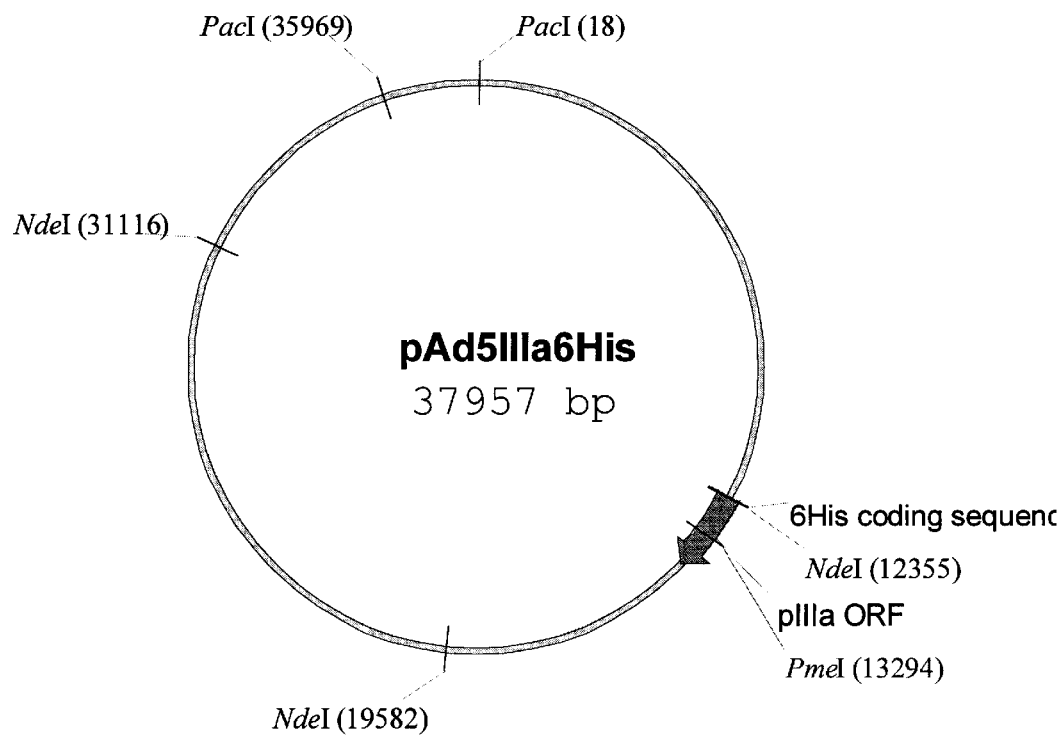
FIG. 3 shows the diagram of plasmid pAd5IIIa6His.

In order to obtain Ad5 genome containing modified gene for pIIIa, the shuttle vector pNEBpIIIa6H was utilized for homologous DNA recombination in *Escherichia coli* BJ5183 with PmeI-digested plasmid DNA pTG36021 as previously described [1]. The plasmid obtained as the result of this recombination was designated pAd5IIIa6His (FIG. 3). Ad vector, Ad5IIIa6His, containing recombinant IIIa gene coding for N-terminal 6His tag was generated by transfection of 293 cells with PacI-digested pAd5IIIa6His by the method described previously [1].

EXAMPLE 3

Confirmation of the Insert of 6His Coding Sequence in Ad Vector Genome

Figure 4:
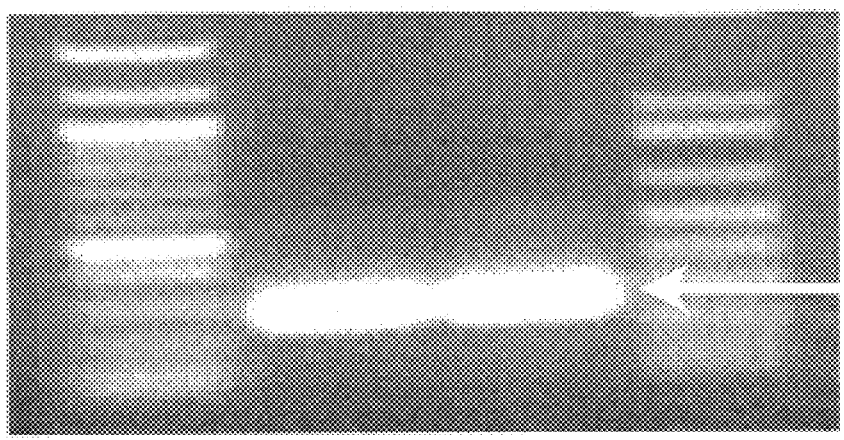
FIG. 4 shows the appearance of a 260 bp DNA fragment after PCR indicating the presence of 6His coding sequence in the pIIIa gene of the modified Ad genome.

PCR was employed to demonstrate the presence of 6His coding sequence in pilIa gene of the Ad genome. Sense primer N6His.U (5'-ATG CAC CAT CAC CAT CAC CAT ATG, SEQ ID No. 6) was design to be complementary to 6His coding sequence. Primer pIIIaN.R (5'-TTC GGC CAG CGC GTT TAC GAT C, SEQ ID No. 4) complementary to the sequence 260 bp downstream of 5'-end of pIIIa gene was used as antisense primer. The lyzate of 293 cell monolayer containing viral plaques 10 days posttrasfection was used as a template for PCR. Appearance of 260 bp DNA fragment after PCR (FIG. 4) indicates the presence of 6His coding sequence in the pIIIa gene of the modified Ad genome.

EXAMPLE 4

Genetic Modification of IX Protein of Ad Capsid

Figure 5:
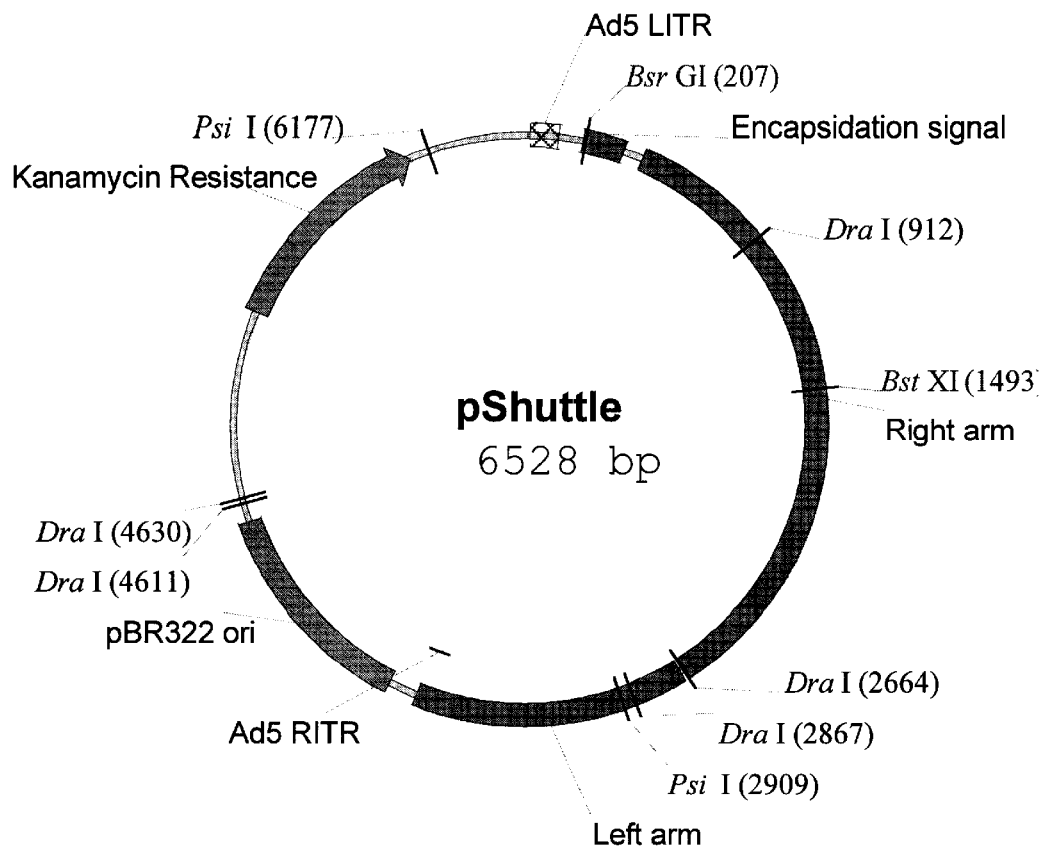
FIG. 5 shows a diagram of plasmid pShuttle.

In order to generate the shuttle vector for incorporation of Flag peptide (Asp Tyr Lys Asp Asp Asp Asp Lys, SEQ ID No. 1) into the C-terminus of the IX protein, AdEasy vector system was utilized [2]. Oligonucleotides FLAGc.U: 5'-CTG CCG ATT ATA AGG ATG ACG ATG ACA AGT (SEQ ID No. 7) and FLAGc.L: 5'-ACT TGT CAT CGT CAT CCT TAT AAT CGG CAG (SEQ ID No. 8) were designed to form DNA duplex coding for Flag peptide. DNA duplex was cloned into DraI site located at 3'-end of pIX coding sequence. Cloning of the Flag oligo was done by ligation of BsrGI-DraI and DraI-BstXI fragments of DNA isolated from pShuttle plasmid (FIG. 5) with oligo duplex and subsequent cloning of the resultant DNA fragment between BsrGI and BstXI sites in pShuttle plasmid. After transformation of E.coli with ligation mix, plasmid clones were analyzed for the presence of Flag-oligo insert by PCR using upper primer designed for the position of 3904 in Ad5 genome (5'-AGT TGA CGG CTC TTT TGG CAC A, SEQ ID No. 9) and FLAGcL as lower primer. PCR-positive clone was then analyzed for the presence of Psi I site, designed inside of the Flag-oligo, by digestion with Psi I.

Figure 6:
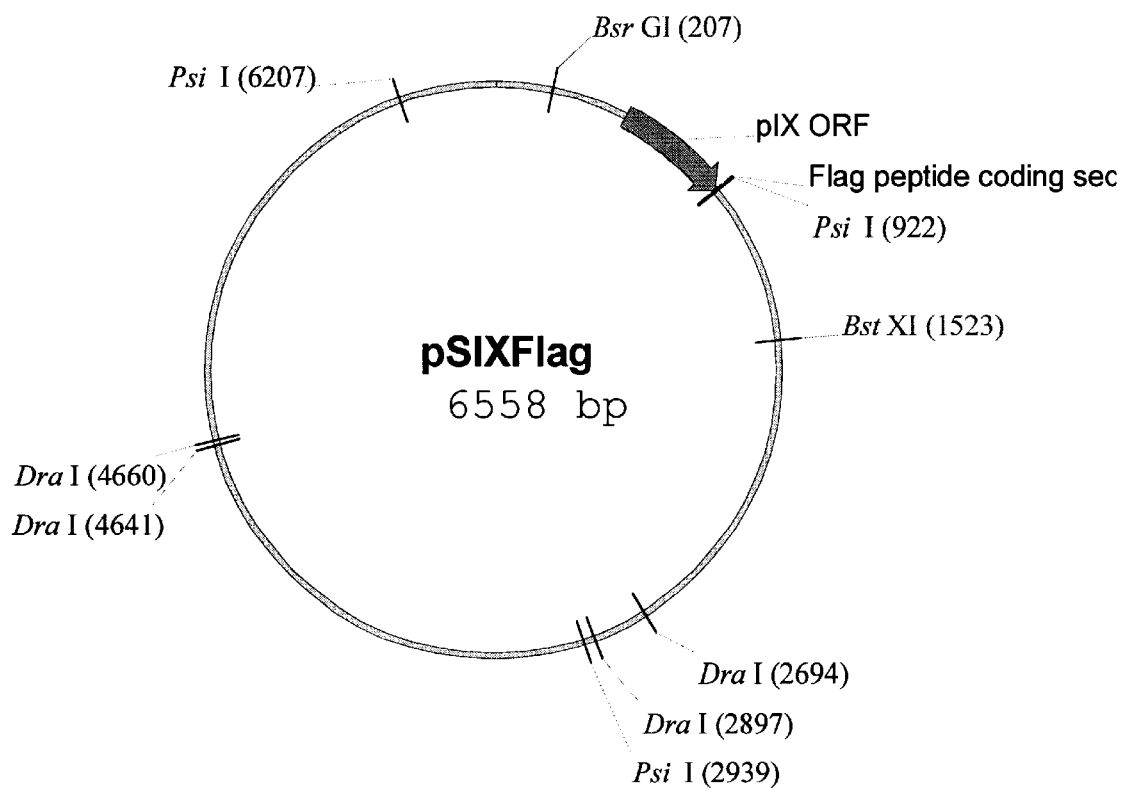
FIG. 6 shows a diagram of plasmid pSIXFlag.
Figure 7:
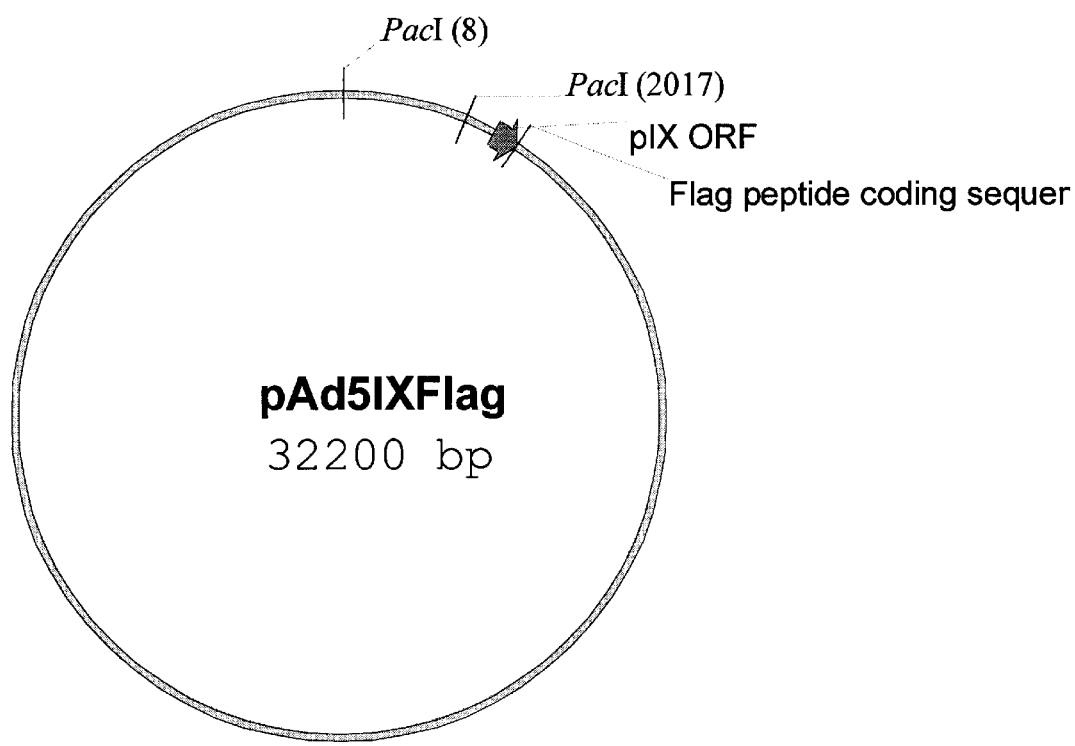
FIG. 7 shows a diagram of plasmid pAd5IXFlag.

After sequence analysis of the correct structure of Flag-oligo cloned into 3'-end of pIX gene the resultant plasmid, pSIXFlag (FIG. 6), was utilized for homologous DNA recombination in Escherichia coli BJ5183 with plasmid DNA pAdEazy1 containing Ad genome as described [2]. The plasmid obtained as the result of this recombination was designated pAd5IXFlag (FIG. 7) and was used to generate Ad vector containing recombinant IX gene coding for C-terminal Flag peptide. Ad vector, Ad5IXFlag, was generated by transfection of 293 cells with PacI-digested pAd5IXFlag by the method described previously [2].

EXAMPLE 5

Confirmation of Flag Peptide Presence in the Adenoviral Capsid

Figure 8:
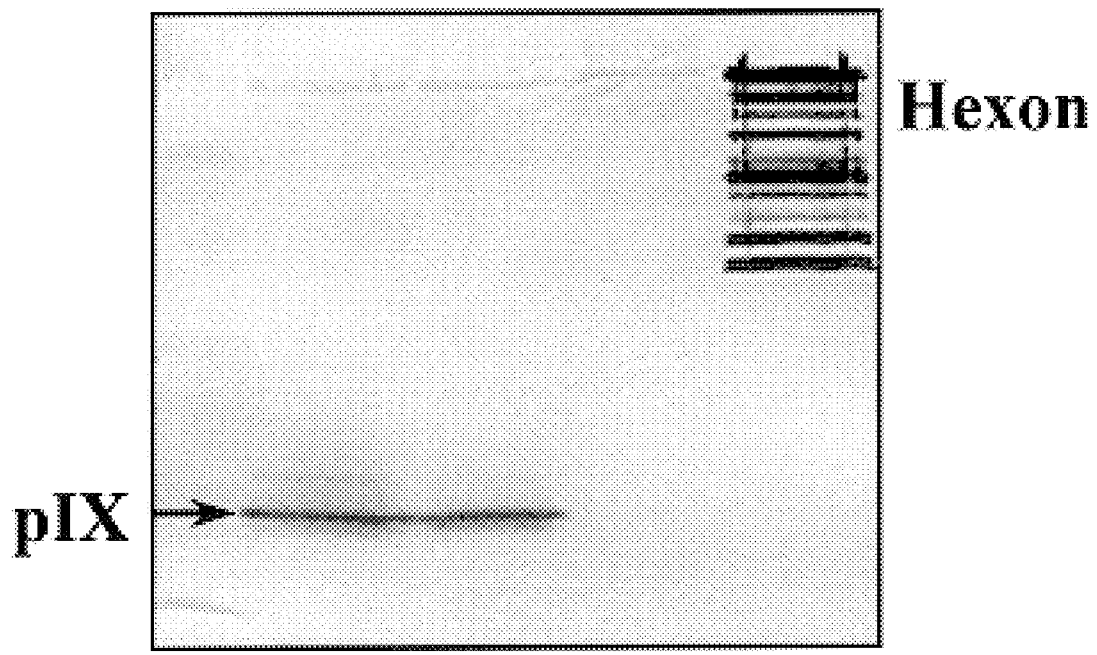
FIG. 8 shows a western blot analysis of Ad vector containing the Flag peptide tag in the IX capsid protein. Viral capsomers from AdpIXFlag or Ad5hexFlag that contains Flag peptide in hexon protein were separated by electrophoresis, transferred onto PVDF membrane and incubated with anti-Flag M2 monoclonal antibody followed by incubation with secondary anti-mouse Ab conjugated with alkaline phosphatase. The presence of protein band of 15 kDa corresponds to the expected molecular weight of protein IX containing Flag peptide.

In order to characterize generated Ad vector for the presence of Flag peptide containing protein IX in the viral capsid, Western blot analysis was done. Virus purified on CsCl gradient was boiled in Lemmli buffer and loaded on SDS-PAGE gel to separate the proteins of viral capsid. Ad vector, Ad5hexFlag, containing Flag peptide in hexon protein was used as a positive control for the Western blot. Viral capsomers separated during electrophoresis were transferred onto PVDF membrane and incubated with anti-Flag M2 MAb followed by incubation with secondary anti-mouse Ab conjugated with alkaline phosphatase. Western blot analysis revealed the presence of protein band of 15 kDa that corresponds to the expected molecular weight of protein IX containing Flag peptide (FIG. 8).

Figure 9:
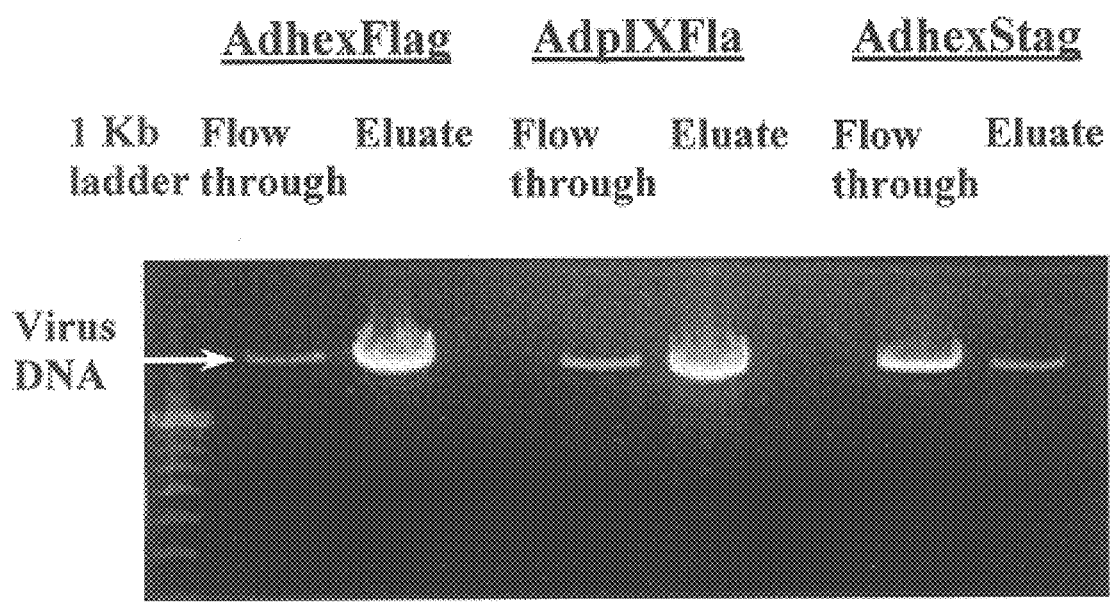
FIG. 9 shows the surface localization of Flag peptide in the context of assembled viral capsid protein IX. Flow through or eluates that bind to an affinity column containing anti-Flag M2 Mab were lyzed by lysis buffer and loaded onto agarose gel in order to visualize viral DNA. Major bands of high molecular viral DNA was visualized in the eluate fractions of Ad5IXFlag and that of positive control AdhexFlag, whereas major amount of viral DNA was found in the flow through fraction of the negative control Adhex-Stag.

To demonstrate the surface localization of Flag peptide in the context of assembled viral capsid of the generated virus, affinity column purification was performed. Ad vectors containing accessible Flag and StrepTag peptides in hexon protein were used respectively as a positive and a negative control for purification. CsCl-purified virus was loaded onto the column containing anti-Flag M2 MAb agarose beads and the column was then washed to remove unbound virus. Virus bound to column was lyzed by incubation of agarose beads with viral lyses buffer (0.6% SDS; 10 mM EDTA; 100 µg/ml Proteinase K) for 10 min. at 56° C. in order to release viral DNA from virions. Virions that passed through the column without binding to M2 MAb (flow through) were lyzed by incubation with lyses buffer as well. Aliquots of flow through and eluate fractions collected throughout the purification of generated Ad5IXFlag as well as the control viruses were loaded onto agarose gel in order to visualize viral DNA. DNA electrophoresis revealed the presence of major bands of high molecular viral DNA in eluate fractions of Ad5IXFlag and positive control virus (FIG. 9). In case of negative control virus containing StrepTag peptide the major amount of viral DNA was found in flow through fraction. These data strongly indicate that Flag peptide incorporated into C terminus of IX protein is displayed on the outer surface of adenoviral capsid and accessible for binding interactions in the context of assembled viral particle.

The following references were cited herein:
1. Chartier et al. (1996) J. Virol. 70:4805–4810.
2. He et al. (1998) Proc Natl Acad Sci USA. 95(5):2509–14.

Any patents or publications mentioned in this specification are indicative of the levels of those skilled in the art to which the invention pran. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art and which are encompassed within the spirit of the invention as defined by the scope of the claims.

What is claimed is:

1. A recombinant adenovirus comprising a modified minor capsid protein gene selected from the group consisting of a minor capsid protein pIIIa gene modified by inserting a DNA sequence encoding a peptide into the 5' end of said pIIIa gene and a minor capsid protein pIX gene modified by inserting a DNA sequence encoding a single chain antibody into the 3' end of said pIX gene.

2. The recombinant adenovirus of claim 1, wherein said peptide is a single chain antibody.

3. The recombinant adenovirus of claim 1, wherein said single chain antibody is directed towards a protein, wherein said protein is specific to a cell type.

4. The recombinant adenovirus of claim 3, wherein said cell type is a tumor cell.

5. The recombinant adenovirus of claim 3, wherein said protein is a cell-surface protein.

6. The recombinant adenovirus of claim 1, wherein the encoded modified capsid protein retains its native display profile.

7. The recombinant adenovirus of claim 1, wherein said adenovirus can mediate coxsackie adenovirus receptor-independent gene transfer to cells expressing targeting ligands to which said peptide or said single chain antibody inserted in said adenovirus can bind.

8. The recombinant adenovirus of claim 1, wherein said recombinant adenovirus further comprises a DNA sequence encoding a therapeutic protein.

9. The recombinant adenovirus of claim 8, wherein said therapeutic protein is a herpes simplex virus-thymidine kinase.

* * * * *

SEQUENCE LISTING

```
<160> NUMBER OF SEQ ID NOS: 9

<210> SEQ ID NO 1
<211> LENGTH: 8
<212> TYPE: PRT
<213> ORGANISM: Unknown
<220> FEATURE:
<221> NAME/KEY: CHAIN
<222> LOCATION:
<223> OTHER INFORMATION: Flag peptide tag

<400> SEQUENCE: 1

Asp Tyr Lys Asp Asp Asp Asp Lys
                5               8
```

```
<210> SEQ ID NO 2
<211> LENGTH: 25
<212> TYPE: DNA
<213> ORGANISM: Artificial Sequence
<220> FEATURE:
<221> NAME/KEY: primer_bind
<223> OTHER INFORMATION: primer pIIIaN.F for introducing six histidine
      tag into the pIIIa protein

<400> SEQUENCE: 2
cgcgaggagg tggctatagg actga                                          25

<210> SEQ ID NO 3
<211> LENGTH: 36
<212> TYPE: DNA
<213> ORGANISM: Artificial Sequence
<220> FEATURE:
<221> NAME/KEY: primer_bind
<223> OTHER INFORMATION: primer pIIIaN6His.L for introducing six
      histidine tag into the pIIIa protein

<400> SEQUENCE: 3
atggtgatgg tgatggtgca tctgatcaga aacatc                              36

<210> SEQ ID NO 4
<211> LENGTH: 22
<212> TYPE: DNA
<213> ORGANISM: Artificial Sequence
<220> FEATURE:
<221> NAME/KEY: primer_bind
<223> OTHER INFORMATION: primer pIIIaN.R for introducing six histidine
      tag into the pIIIa protein

<400> SEQUENCE: 4
ttcggccagc gcgtttacga tc                                             22

<210> SEQ ID NO 5
<211> LENGTH: 32
<212> TYPE: DNA
<213> ORGANISM: Artificial Sequence
<220> FEATURE:
<221> NAME/KEY: primer_bind
<223> OTHER INFORMATION: primer pIIIaN6His.U for introducing six
      histidine tag into the pIIIa protein

<400> SEQUENCE: 5
caccatcacc atcaccatat gcaagacgca ac                                  32

<210> SEQ ID NO 6
<211> LENGTH: 24
<212> TYPE: DNA
<213> ORGANISM: Artificial Sequence
<220> FEATURE:
<221> NAME/KEY: primer_bind
<223> OTHER INFORMATION: Sense PCR primer N6His.U complementary to 6His
      coding sequence

<400> SEQUENCE: 6
atgcaccatc accatcacca tatg                                           24

<210> SEQ ID NO 7
<211> LENGTH: 30
<212> TYPE: DNA
<213> ORGANISM: Artificial Sequence
<220> FEATURE:
<221> NAME/KEY: 
<223> OTHER INFORMATION: Oligonucleotide FLAGc.U designed to form DNA
      duplex coding for Flag peptide
```

-continued

```
<400> SEQUENCE: 7
ctgccgatta taaggatgac gatgacaagt                                          30

<210> SEQ ID NO 8
<211> LENGTH: 30
<212> TYPE: DNA
<213> ORGANISM: Artificial Sequence
<220> FEATURE:
<221> NAME/KEY:
<223> OTHER INFORMATION: Oligonucleotide FLAGc.L designed to form DNA
      duplex coding for Flag peptide

<400> SEQUENCE: 8
acttgtcatc gtcatcctta taatcggcag                                          30

<210> SEQ ID NO 9
<211> LENGTH: 22
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 9
agttgacggc tcttttggca ca                                                  22
```